United States Patent [19]

Frater et al.

[11] 4,329,488
[45] May 11, 1982

[54] PROPIONIC ACID ESTERS AND HERBICIDAL USE THEREOF

[75] Inventors: Georg Frater, Greifensee; Jean Wenger, Uster, both of Switzerland

[73] Assignee: Hoffmann-La Roche Inc., Nutley, N.J.

[21] Appl. No.: 213,282

[22] Filed: Dec. 5, 1980

[51] Int. Cl.³ .............................................. C07C 69/76
[52] U.S. Cl. ...................................... 560/62; 560/23; 560/63; 71/108; 71/109; 71/111
[58] Field of Search ...................... 560/62, 63; 71/100, 71/102, 116, 108

[56] References Cited

U.S. PATENT DOCUMENTS

| | | | |
|---|---|---|---|
| 3,954,442 | 5/1976 | Becker et al. | 560/62 |
| 3,989,737 | 11/1976 | Sawaki | 560/62 |
| 4,033,754 | 7/1977 | Sawaki | 560/193 |
| 4,070,177 | 1/1978 | Nishiyama et al. | 560/62 |
| 4,175,947 | 11/1979 | Koch et al. | 560/62 |
| 4,200,587 | 4/1980 | Suchy | 560/62 |
| 4,227,009 | 10/1980 | Koch et al. | 560/62 |
| 4,270,948 | 6/1981 | Takahashi et al. | 560/62 |

*Primary Examiner*—Paul J. Killos
*Attorney, Agent, or Firm*—Jon S. Saxe; Bernard S. Leon; James H. Callwood

[57] ABSTRACT

Propionic acid esters of the general formula

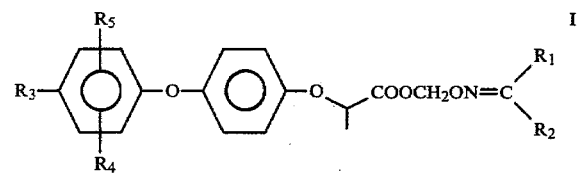

wherein $R_1$ is hydrogen, alkyl of from 1 to 6 carbon atoms or phenyl, $R_2$ is alkyl of from 1 to 6 carbon atoms, alkenyl of from 2 to 6 carbon atoms, alkynyl of from 2 to 6 carbon atoms or phenyl, or $R_1$ and $R_2$ together with the carbon atom to which they are attached form a cycloalkane ring containing 4 to 10 carbon atoms which can be mono-, di- or trisubstituted with alkyl of from 1 to 3 carbon atoms, $R_3$ represents a halogen, trifluoromethyl or nitro, and $R_4$ and $R_5$ each represent a hydrogen or halogen atom, processes for their manufacture, herbicidal compositions containing these compounds as the active ingredient and methods of use of the herbicidal compositions are disclosed.

23 Claims, No Drawings

PROPIONIC ACID ESTERS AND HERBICIDAL USE THEREOF

BACKGROUND OF THE INVENTION

In U.S. Pat. No. 4,200,587, 2-[p-(p-substituted phenoxy)phenoxy]propionyl oximes of the general formula

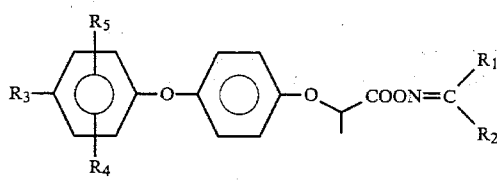

wherein $R_1$ is hydrogen, alkyl of from 1 to 6 carbon atoms or phenyl; $R_2$ is hydrogen, alkyl of from 1 to 6 carbon atoms, alkenyl of from 2 to 6 carbon atoms, alkynyl of from 2 to 6 carbon atoms or phenyl; or $R_1$ and $R_2$ together are cyclohexane which can, optionally, be mono-substituted, disubstituted or trisubstituted with alkyl of from 1 to 3 carbon atoms, $R_3$ is hydrogen, fluorine, chlorine, bromine, trifluoromethyl or nitro and $R_4$ and $R_5$ represent hydrogen or chlorine, with the proviso that $R_1$ and $R_2$ are not both hydrogen, are disclosed as herbicides.

Further, in German DOS No. 2,262,402 compounds of the general formula

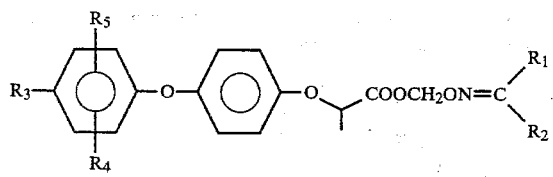

wherein $R_1$ and $R_2$ are aromatic, aliphatic, cycloaliphatic, araliphatic or heterocyclic hydrocarbon groups optionally having one or more substituents; $R_1$ can also be hydrogen; $R_1$ and $R_2$ together with the carbon atom can be nitrogen- and/or oxygen-containing cycloaliphatic hydrocarbon groups; $R_3$ is hydrogen or alkyl, X is hydrogen, alkyl, alkoxy, haloalkyl or halogen, and n is an integer from 1 to 3, are disclosed as herbicides.

SUMMARY OF THE INVENTION

This invention is directed to propionic acid esters of the formula

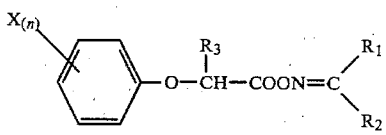

wherein $R_1$ represents a hydrogen atom, an alkyl group containing 1 to 6 carbon atoms or a phenyl group, $R_2$ represents an alkyl group containing 1 to 6 carbon atoms, an alkenyl group containing 2 to 6 carbon atoms, an alkynyl group containing 2 to 6 carbon atoms or a phenyl group or $R_1$ and $R_2$ together with the carbon atom to which they are attached form a cycloalkane ring containing 4 to 10 carbon atoms which, if desired, can be mono-, di- or trisubstituted with alkyl containing 1 to 3 carbon atoms, $R_3$ represents a halogen atom or a trifluoromethyl or nitro group and $R_4$ and $R_5$ each represent a hydrogen or halogen atom, as well as processes for their preparation. This invention is also directed to herbicidal compositions containing, as the active ingredient, a compound of formula I and methods for the use of these herbicidal compositions.

DETAILED DESCRIPTION OF THE INVENTION

The invention is directed to propionic acid esters of the formula

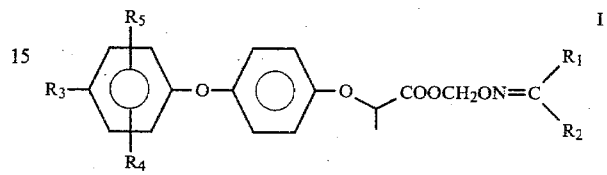

wherein $R_1$ is hydrogen atom, alkyl of from 1 to 6 carbon atoms or phenyl, $R_2$ is alkyl of from 1 to 6 carbon atoms, alkenyl of from 2 to 6 carbon atoms, alkynyl of from 2 to 6 carbon atoms or phenyl, or $R_1$ and $R_2$ together with the carbon atom to which they are attached form a cycloalkane ring containing 4 to 10 carbon atoms which can be mono-, di- or trisubstituted with alkyl containing 1 to 3 carbon atoms, $R_3$ represents a halogen, trifluoromethyl or nitro, and $R_4$ and $R_5$ each represent a hydrogen or halogen atom.

This invention is also directed to processes for the preparation of the compounds of formula I has well as herbicidal compositions which contain, as the active ingredient, a compound of formula I, and methods for their use. The compounds have both pre-emergence and post-emergence herbicidal activity.

The term alkyl encompasses both straight- and branched-chain hydrocarbon groups containing from 1 to 3 or 1 to 6 carbon atoms such as methyl, ethyl, propyl, isopropyl, butyl, isobutyl, t-butyl and the like.

The terms alkenyl and alkynyl encompass both straight- and branched-chain unsaturated hydrocarbon groups of from 2 to 6 carbon atoms such as allyl, butenyl, isobutenyl, pentenyl, isopentyl and the like and propargyl, butynyl, isobutynyl, pentynyl and the like. Preferred alkynyl groups are 1-propynyl, butynyl and isobutynyl.

The term halogen encompasses fluorine, chlorine, bromine and iodine and preferably chlorine, bromine and iodine.

The cycloalkane ring preferably contains 4 to 7 carbon atoms, especially 4 to 6 carbon atoms.

Preferred compounds of formula I are those in which $R_1$ is methyl or ethyl, those in which $R_2$ is methyl, ethyl or phenyl, those in which $R_3$ is chlorine or trifluoromethyl, those in which $R_4$ is hydrogen and those in which $R_5$ is hydrogen. The compounds of formula I in which $R_1$ and $R_2$ together with the carbon atom to which they are attached form a cycloalkane ring which may be substituted with alkyl are also preferred.

Particularly preferred compounds of the formula I are:

2-[p-[(α,α,α-Trifluoro-p-tolyl)oxy]phenoxy]-propionic acid [[(isopropylideneamino)oxy]methyl]ester and 2-[p-(p-chlorophenoxy)phenoxy]-propionic acid [[(isopropylideneamino)oxy]methyl]ester.

Examples of other compounds of formula I are:

2-[p-(2,4-Dichlorophenoxy)phenoxy]-propionic acid [[(isopropylideneamino)oxy]methyl]ester, 2-[p-(2,4-dichlorophenoxy)phenoxy]-propionic acid [[(α-methyl-benzylideneamino)oxy]methyl]ester, 2-[p-[(α,α,α-trifluoro-p-tolyl)oxy]phenoxy]-propionic acid [[(sec.butylideneamino)oxy]methyl]ester, 2-[p-[(α,α,α-trifluoro-p-tolyl)oxy]phenoxy]-propionic acid [[(1-pentyl-hexylideneamino)oxy]methyl]ester, 2-[p-[(α,α,α-trifluoro-p-tolyl)oxy]phenoxy]-propionic acid [[(1,3-dimethyl-2-butylideneamino)oxy]methyl]ester, 2-[p-[(α,α,α-trifluoro-p-tolyl)oxy]phenoxy]-propionic acid [[(α-methyl-benzylideneamino)oxy]methyl]ester, 2-[p-[(α,α,α-trifluoro-p-tolyl)oxy]phenoxy]-propionic acid [[(cyclohexylideneamino)oxy]methyl]ester, 2-[p-[(α,α,α-trifluoro-p-tolyl)oxy]phenoxy]-propionic acid [[(cyclopentylideneamino)oxy]methyl]ester, 2-[p-[(α,α,α-trifluoro-p-tolyl)oxy]phenoxy]-propionic acid [[(cycloheptylideneamino)oxy]methyl]ester, 2-[p-[(α,α,α-trifluoro-p-tolyl)oxy]phenoxy]-propionic acid [[(benzylideneamino)oxy]methyl]ester, 2-[p-(p-bromophenoxy)phenoxy]-propionic acid [[(isopropylideneamino)oxy]methyl]ester, 2-[p-(p-nitrophenoxy)phenoxy]-propionic acid [[(isopropylideneamino)oxy]methyl]ester and lower alkyl-substituted derivatives of the aforementioned cyclopentylideneamino, cyclohexylideneamino and cycloheptylideneamino compounds.

Especially preferred are the D-isomers of the compounds of formula I and consequently the D-isomers of the aforementioned individually named compounds.

The compounds of formula I are prepared by one of the procedures described below.

A. The reaction of a salt of an acid of the formula

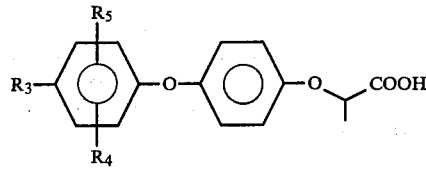    II wherein $R_3$, $R_4$ and $R_5$ have the same significance as in formula I above, with a compound of the general formula

    III wherein $R_1$ and $R_2$ have the same significance given for formula I and X represents a leaving group.

The term salt of an acid encompasses, for example, an alkali metal salt such as, for example, the sodium, potassium or lithium salt, an alkaline earth metal salt such as, for example, the magnesium, calcium or barium salt, a salt of an organic base such as, for example, a mono-, di- or trialkylammonium salt or a pyridinium salt, or the ammonium salt.

The leaving group denoted by X in the compounds of formula III is, for example, a chlorine, bromine or iodine atom, a tosyloxy or mesyloxy group, a hydroxyl group in free or esterified form or one of the following groups:

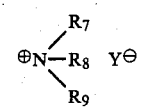    (a)

wherein $R_7$, $R_8$ and $R_9$, which can be the same or different, each represent an alkyl group, especially an alkyl group containing 1 to 6 carbon atoms, or two of $R_7$, $R_8$ and $R_9$ together also form a $C_4$–$C_7$-alkylene group and $Y^\ominus$ represents an anion, for example, chlorine, bromine or iodine anion or a hydroxyl or sulphate anion;

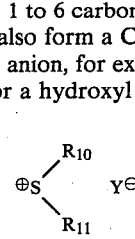    (b)

wherein $R_{10}$ and $R_{11}$, which can be the same or different, each represent an alkyl group, especially an alkyl group containing 1 to 6 carbon atoms, and $Y^\ominus$ has the significance given above;

    (c)

wherein $R_{12}$ represents a lower alkyl, an aryl or a heteroaryl group and n stands for 1 or 2.

The reaction of a salt of an acid of formula II with a compound of formula III is preferably carried out in a suitable inert solvent at about −10° C. to 220° C., preferably at room temperature or at an elevated temperature. The preferred temperature range is between 20° C. and 70° C. The reaction is carried out, for example, in the presence of an inert solvent such as benzene, toluene, petroleum ether, dimethylformamide, tetrahydrofuran, acetonitrile, N-methyl-2-pyrrolidone, tetramethylurea, dimethoxyethane, diglycol dimethyl ether or hexamethylphosphoric acid triamide.

B. The reaction of a compound of the general formula

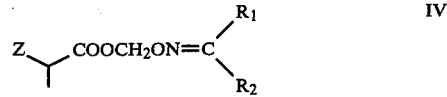    IV wherein Z represents a leaving group and $R_1$ and $R_2$ have the same significance as given in formula I above, with a compound of the formula

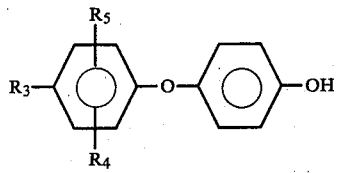    V wherein $R_3$, $R_4$ and $R_5$ have the same significance as in formula I above, or with an alkali metal salt thereof, if necessary in the presence of a base.

The leaving group denoted by Z in compounds of formula IV is, for example, a leaving group mentioned hereinbefore in connection with X or a hydroxy group activated by reaction with triphenylphosphine and azodicarboxylic acid or an ester thereof, especially azodicarboxylic acid diethyl ester, see, e.g. Bull. Chem. Soc. Japan 46, 2833 (1973) or Angew. Chem. 88, 111 (1976).

A compound of formula IV is reacted with a compound of formula V or an alkali metal salt of a compound of formula V by known procedures. The reaction is conveniently carried out in an inert organic solvent such as a hydrocarbon, e.g. benzene or toluene, an ether, e.g. diethyl ether, tetrahydrofuran or dimethoxyethane, or hexamethylphosphoric acid triamide. Temperature and pressure are not critical. The reaction is preferably carried out at a temperature of from about −20° C. to the reflux temperature of the reaction mixture, preferably between −10° C. and 30° C.

C. The reaction of a compound of the formula

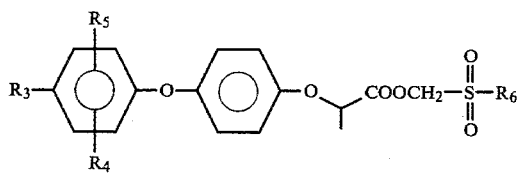

wherein $R_6$ represents lower alkyl, aryl or heteroaryl and $R_3$, $R_4$ and $R_5$ have the same significance as in formula I above, with an oxime of the formula $$R_1R_2CNOH \qquad \text{VII}$$

wherein $R_1$ and $R_2$ have the same significance as in formula I above, or with an alkali metal salt thereof in the presence of a base.

The term lower alkyl refers to alkyl groups containing, especially, 1 to 6 carbon atoms.

The term aryl encompasses phenyl, phenyl substituted with 1 to 3 lower alkyl groups, as well as naphthyl. The lower alkyl groups can be the same or different.

The term heteroaryl encompasses pyridyl, imidazolyl, thiazolyl and thiophenyl groups.

In this reaction, a compound of formula VI is reacted with an oxime of formula VII in the presence of a base, for example an alkali metal carbonate. The compound of formula VI can be dissolved in an inert organic solvent such as a chlorinated hydrocarbon, for example dichloromethane, chloroform, carbon tetrachloride or trichloroethane, an ether or ether-like compound, such as tetrahydrofuran, diethyl ether, diisopropyl ether, dimethoxyethane or dioxan, an aromatic hydrocarbon, for example benzene, toluene or xylene, or dimethylformamide, dimethylsulphoxide or hexamethylphosphoric acid triamide. The oxime of formula VII is then added to the reaction mixture in the form of an alkali metal salt.

The reaction can be carried out over a temperature range of from about 0° C. to the boiling temperature of the reaction mixture with the preferred temperature range being from 0° C. to about 50° C.

After a short time, e.g. a few minutes, the reaction is normally complete. The reaction mixture is conveniently poured into water and the product extracted with an organic solvent, e.g. ethyl acetate. The solvent is evaporated and the residue is purified by, e.g. recrystallization or chromatography.

The starting materials of formulae II, III, IV, V and VII belong to known classes of compounds.

Compounds of formula VI can be prepared by oxidation of compounds of the formula

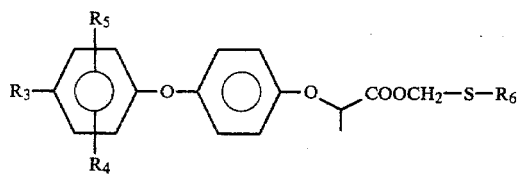

wherein $R_3$, $R_4$, $R_5$ and $R_6$ have the same significance as given above. The oxidation can be carried out, for example, using hydrogen peroxide.

Compounds of formulae VI and VIII can be prepared by analogous procedures to those described in DOS No. 2,617,804. The racemic mixtures of these compounds can be resolved by employing well-known conventional procedures.

The racemates and optical antipodes of the compounds of formulae VI and VIII wherein $R_6$ is a heteroaryl group are novel. In addition, the D-isomers of the compounds of formulae VI and VIII wherein $R_6$ is lower alkyl, e.g. methyl, or aryl, e.g. phenyl or halophenyl, are also novel.

The novel compounds of formulae VI and VIII can be prepared by reacting the racemate or the D-isomer of a compound of formula II with a compound of the formula $$HO-CH_2-S-R_6 \qquad \text{IX}$$

The reaction is suitably carried out in an inert organic solvent, e.g. chloroform or dimethyl sulfoxide, in the presennce of dicyclohexylcarbodiimide. The compound of formula VIII can then be oxidized, e.g. with hydrogen peroxide, to a compound of formula VI.

Starting materials of formula VI and VIII which are particularly preferred include:

D-2-[p-(p-bromophenoxy)phenoxy]-propionic acid methylthiomethyl ester,

D-2-[p-(p-fluorophenoxy)phenoxy]-propionic acid methylthiomethyl ester,

D-2-[p-(p-nitrophenoxy)phenoxy]-propionic acid methylthiomethyl ester and

D-2-[p-(p-trifluoromethylphenoxy)phenoxy]-propionic acid methylthiomethyl ester as well as the corresponding sulphonyl compounds.

The above starting materials to formulae VI and VIII, especially the D-isomers thereof, are also useful as herbicides since they have a spectrum of activity similar to the compounds of formula I. Compared to the corresponding racemates, the D-isomers have a lower phytotoxicity to, e.g. cotton and soybeans. They can be used for the manufacture of herbicidal compositions in the same manner as described hereinafter for the compounds of formula I.

Since the substituted propionic acid esters of formula I have asymmetric carbon atoms in the α-position to the carbonyl group, these compounds can exist in optically active isomeric forms. In fact, these esters can have more than one asymmetric carbon atom. The racemic compounds can be resolved in their dextrorotatory and laevorotatory isomers using known procedures as, for example, that described in Industrial and Engineering Chemistry 60(8), 12-28 (1968). The racemic mixtures as well as the isomers all have herbicidal activity with the D-isomer having the highest activity followed by the racemic mixture and the L-isomer. For example, it has been found that the D-isomer of 2-[p-[(α,α,α-trifluoro-p-tolyl)oxy]phenoxy]-propionic acid[[(isopropylideneamino)oxy]methyl]ester has a higher activity than the racemic mixture.

The isomers can also be manufactured by synthesis from corresponding optically active starting materials. Such starting materials are especially preferred.

In addition, and as a result of the nitrogen-carbon double bond in the oxim group

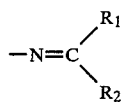

it is also possible to have in each case two geometric isomers when $R_1$ and $R_2$ are different. These isomers, the syn- and anti-form, can also be isolated in certain cases.

This invention is also directed to herbicidal compositions which comprise inert carrier material and, as the active ingredient, one or more compounds of formula I. These herbicidal compositions suitably contain, as the inert carrier material, at least one of the following ingredients: carrier materials, wetting agents, inert diluents and solvents.

The compounds of formula I are, in general, water-insoluble. Thus, the usual methods of formulation of insoluble materials can be followed. For example, the compounds can be dissolved in a water-immiscible solvent such as a high-boiling hydrocarbon which conveniently contains dissolved emulsifiers so that the solution acts as a self-emulsifiable oil when added to water.

The compounds of formula I can also be mixed with a wetting agent, with or without an inert diluent, to form a wettable powder which is soluble or dispersible in water. The compounds can alternatively be mixed with an inert diluent to form a solid or pulverulent product.

Suitable inert diluents are solid inert media including pulverulent or finely divided solids such as clays, sand, talc, mica, fertilizers and the like. The resulting compositions can be either dusts or materials of relatively large particle size.

Wetting agents, suitable for use with the compounds of this invention, can be anionic, cationic or nonionic.

Examples of anionic wetting agents include soaps, fatty sulfate esters such as dodecyl sodium sulfate, octadecyl sodium sulfate and cetyl sodium sulfate, fatty aromatic sulfonates such as alkylbenzene-sulfonates and butylnaphthalene-sulfonates, and the more complex fatty sulfonates such as the amide condensation products of oleic acid and N-methyltaurine or the sodium sulfonate of dioctyl succinate.

Examples of cationic wetting agents include cetyl-trimethylammonium bromide and the like.

Examples of nonionic wetting agents include, for example, condensation products of fatty acids, fatty alcohols or fatty substituted phenols with ethylene oxides; fatty acid esters and ethers of sugars or polyhydric alcohols; condensation products of sugars or polyhydric alcohols with ethylene oxide; and block copolymers of ethylene oxide and propylene oxide.

The herbicidal compositions of this invention can also be used in aerosol form using, in addition to the propellant gas, carrier material comprising a co-solvent and a wetting agent. Suitable propellant gases include the polyhalogenated alkanes such as dichlorodifluoromethane.

The herbicidal compositions of this invention can also contain other active ingredients such as synergistic agents, insecticides, acaricides, bactericides, other herbicides, fungicides, plant growth regulators and fertilizers. Such combination preparations are suitable for increasing the activity or for broadening the spectrum of activity.

The compounds of this invention are useful as both pre-emergent and post-emergent herbicides. They are particularly suitable in combatting weeds such as slender foxtail (*Alopecurus myosuroides*) and types of millet such as cock's foot (*Echinochloa crus-galli*), great foxtail millet (*Setaria fagerii*) and hair-like millet (*Panicum capillare*) in cereals. They are suitable for use against these weeds especially in cereals such as barley, oats and wheat and in rice, cotton, soya, sugar beet and vegetable crops.

The pre-emergent and post-emergent herbicidal compositions of this invention are especially preferred for combatting weeds in sugar beet crops. For example, 2-[p-[(α,α,α-trifluoro-p-tolyl)oxy]phenoxy]-propionic acid[[(isopropylideneamino)oxy]methyl]ester applied at a concentration of 1.25 kg/ha is sufficiently active against weeds without damaging the sugar beet crop.

In general, the compounds of this invention are effective as herbicides when applied at a concentration of about 0.1 to about 6 kg/ha with the preferred concentration range being from about 0.6 to about 2.0 kg/ha. An especially preferred application rate is from about 1 to about 1.5 kg/ha.

The utility in corn crops of compounds of formula I wherein $R_3$ is trifluoromethyl is limited since these compounds are somewhat phytotoxic. However, these compounds are particularly suitable for combatting weeds in rice, cotton, soya, sugar beet and vegetable crops.

The herbicidal compositions of this invention can be in the form of concentrates suitable for storage or shipment. Such compositions can contain, e.g. from about 2% to about 90% by weight, based on the weight of the total composition, of one or more of the active compounds of this invention. These concentrates can be diluted, with the same or different inert carrier material, to concentrations which are suitable for actual use. Ready-to-use compositions can contain concentrations of from 0.05% to 80% by weight of the active ingredient. Particularly preferred concentrations of active ingredients in the herbicidal compositions of this invention are from about 2% to about 8% by weight and from about 50% to about 80% by weight.

The following Examples illustrate the present invention.

EXAMPLE 1

36 g of 2-[p-[(α,α,α-trifluoro-p-tolyl)oxy]-phenoxy]-propionic acid [(methylsulphonyl)methyl]ester are dissolved in 20 ml of tetrahydrofuran. A mixture of 0.35 g of acetone oxime sodium salt, dissolved in 20 ml of dimethylformamide, is added to this solution and the mixture is stirred at room temperature for 2 minutes. The mixture is poured into water, extracted with ethyl acetate and washed neutral with water. The ethyl acetate is evaporated and the residue is then chromatographed on 100 g of silica gel with hexane/ethyl acetate (8:2). The eluate is evaporated and the residue is recrystallised from ether/hexene. The resulting 2-[p-[(α,α,α-trifluoro-p-tolyl)oxy]phenoxy]-propionic acid [[(isopropylideneamino)oxy]methyl]ester melts at 76°–77° C.

In analogous procedures, the following compounds are prepared:

(a) from D-2-[p-[(α,α,α-trifluoro-p-tolyl)oxy]phenoxy]-propionic acid [(methylsulphonyl)methyl]ester and acetone oxime sodium salt there is obtained D-2-[p-[(α,α,α-trifluoro-p-tolyl)oxy]phenoxy]-propionic acid [[(isopropylideneamino)oxy]methyl]ester; melting point 80°–85° C.; $[α]_D^{22} = +11.62°(c=1.25\%$ in chloroform);

(b) from D-2-[p-[(α,α,α-trifluoro-p-tolyl)oxy]phenoxy]-propionic acid [(methylsulphonyl)methyl]ester and acetophenone oxime sodium salt there is obtained D-2-[p-[(α,α,α-trifluoro-p-tolyl)oxy]phenoxy]-propionic acid [[(α-methyl-benzylideneamino)oxy]methyl]ester; melting point 63°–64° C.; $[α]_D^{22} = -13.64°(c=0.75\%$ in chloroform);

(c) from D-2-[p-(p-chlorophenoxy)phenoxy]-propionic acid [(methylsulphonyl)methyl]ester and acetone oxime sodium salt there is obtained D-2-[p-(p-chlorophenoxy)-phenoxy]-propionic acid [[(isopropylideneamino)oxy]-methyl]ester; $n_D^{20}=1.5480$; $[α]_D^{22} = +13.58°(c=1.93\%$ in chloroform);

(d) from 2-[p-(o,p-dichlorophenoxy)phenoxy]-propionic acid [(methylsulphonyl)methyl]ester and acetone oxime sodium salt there is obtained 2-[p-(o,p-dichlorophenoxy)phenoxy]-propionic acid [[(isopropylideneamino)oxy]-methyl]ester; $n_D^{22}=1.5557$.

(e) from 2-[p-(o,p-dichlorophenoxy)phenoxy]-propionic acid [(methylsulphonyl)methyl]ester and acetophenone oxime sodium salt there is obtained 2-[p-(o,p-dichlorophenoxy)phenoxy]-propionic acid [[(α-methyl-benzylideneamino)oxy]methyl]ester; melting point 66°–67° C.;

(f) from D-2-[p-(p-bromophenoxy)phenoxy]-propionic acid [(methylsulphonyl)methyl]ester and acetone oxime sodium salt there is obtained D-2-[p-(p-bromophenoxy)-phenoxy]-propionic acid [[(isopropylideneamino)oxy]-methyl]ester; $n_D^{20}=1.5598$; $[α]_D^{22} = +11.92°(c=1.15\%$ in chloroform);

(g) from D-2-[p-(p-iodophenoxy)phenoxy]-propionic acid [(methylsulphonyl)methyl]ester and acetone oxime sodium salt there is obtained D-2-[p-(p-iodophenoxy)-phenoxy]-propionic acid [[(isopropylideneamino)oxy]-methyl]ester; melting point 40°–43° C.; $[α]_D^{22} = +8.60°(c=0.90\%$ in chloroform);

(h) from D-2-[p-[(α,α,α-trifluoro-p-tolyl)oxy]-phenoxy]-propionic acid [(methylsulphonyl)methyl]ester and cyclopentanone oxime sodium salt there is obtained D-2-[p-[(α,α,α-trifluoro-p-tolyl)oxy]-phenoxy]-propionic acid [[(cyclopentylideneamino)oxy]methyl]ester; melting point 43°–45° C.; $[α]_D^{22} = +7.52°(c=2.28\%$ in chloroform);

(i) from D-2-[p-[(α,α,α-trifluoro-p-tolyl)oxy]phenoxy]-propionic acid [(methylsulphonyl)methyl]ester and cyclohexanone oxime sodium salt there is obtained D-2-[p-[(α,α,α-trifluoro-p-tolyl)oxy]-phenoxy]-propionic acid [[(cyclohexylideneamino)oxy]methyl]ester; melting point 71°–73° C.; $[α]_D^{22} = +5.55°(c=1.49\%$ in chloroform);

(j) from D-2-[p-[(α,α,α-trifluoro-p-tolyl)oxy]phenoxy]-propionic acid [(methylsulphonyl)methyl]ester and cycloheptanone oxime sodium salt there is obtained D-2-[p-[(α,α,α-trifluoro-p-tolyl)oxy]-phenoxy]-propionic acid [[(cycloheptylideneamino)oxy]methyl]ester; melting point ca 30° C.; $[α]_D^{22} = +6.00°(c=1.96\%$ in chloroform);

(k) from D-2-[p-[(α,α,α-trifluoro-p-tolyl)oxy]phenoxy]-propionic acid [(methylsulphonyl)methyl]ester and 3,3,5-trimethylcyclohexanone oxime sodium salt there is obtained D-2-[p-[(α,α,α-trifluoro-p-tolyl)oxy]-phenoxy]-propionic acid [[(3,3,5-trimethylcyclohexylideneamino)oxy]methyl]ester; $n_D^{20}=1.5062$; $[α]_D^{22} = +6.86°(c=2.73\%$ in chloroform);

(l) from D-2-[p-[(α,α,α-trifluoro-p-tolyl)oxy]phenoxy]-propionic acid [(methylsulphonyl)methyl]ester and benzaldoxime sodium salt there is obtained D-2-[p-[(α,α,α-trifluoro-p-tolyl)oxy]phenoxy]-propionic acid [[(benzylideneamino)oxy]methyl]ester; melting point 65°–66° C.; $[α]_D^{22} = -16.34°(c=1.60\%$ in chloroform);

(m) from D-2-[p-[(α,α,α-trifluoro-p-tolyl)oxy]phenoxy]-propionic acid [(methylsulphonyl)methyl]ester and ethyl methyl ketoxime sodium salt there is obtained D-2-[p-[(α,α,α-trifluoro-p-tolyl)oxy]phenoxy]-propionic acid [[(sec.butylideneamino)oxy]methyl]ester; melting point 38°–40° C.; $[α]_D^{22} = +10.34°(c=2.36\%$ in chloroform);

(n) from D-2-[p-[(α,α,α-trifluoro-p-tolyl)oxy]phenoxy]-propionic acid [(methylsulphonyl)methyl]ester and dipentyl ketoxime sodium salt there is obtained D-2-[p-[(α,α,α-trifluoro-p-tolyl)oxy]-phenoxy]-propionic acid [[(1-pentyl-hexylideneamino)oxy]methyl]ester; $n_D^{20}=1.4913$; $[α]_D^{22} = +11.71°(c=3.27\%$ in chloroform);

(o) from D-2-[p-[(α,α,α-trifluoro-p-tolyl)oxy]phenoxy]-propionic acid [(methylsulphonyl)methyl]ester and methyl (2-methyl-1-propenyl) ketoxime sodium salt there is obtained D-2-[p-[(α,α,α-trifluoro-p-tolyl)oxy]-phenoxy]-propionic acid [[(1,3-dimethyl-2-butenylideneamino)oxy]methyl]ester; melting point 52°–54° C.; $[α]_D^{22} = -5.75°(c=0.78\%$ in chloroform).

EXAMPLE 2

A solution of 10 g (0.0307 mol) of D-2-[p-[(α,α,α-trifluoro-p-tolyl)oxy]phenoxy]-propionic acid in 100 ml of dimethylformamide is added dropwise while stirring to a suspension of 1.5 g of 55% sodium hydride dispersion (0.0307 mol) in 20 ml of dimethylformamide. After completion of the addition, the mixture is stirred at room temperature until the hydrogen evolution has stopped. The mixture is stirred for a further 15 minutes and there are added thereto 15 g (0.048 mol) of N-[(isopropylideneamino)oxy]-N-methyl-piperidinium iodide and 0.5 g of 15-crown-5 (the polyethylene ether-crown compound with an 15-ring containing 5 oxygen atoms). After stirring at 110° C. for 2 hours, the mixture is poured into 500 ml of water and extracted three times with 300 ml of ethyl acetate each time. The ethyl acetate extracts are combined, washed twice with 200 ml of water each time and then evaporated, the residue being subsequently recrystallised from diethyl ether/n-hexane. There are obtained 8.0 g of D-2-[p-[(α,α,α-trifluoro-p-tolyl)oxy]-phenoxy]-propionic acid [[(isopropylideneamino)oxy]-methyl]ester which melts at 85°–86° C.; $[α]_D^{20} = +11.3°(c=1.2\%$ in chloroform).

EXAMPLE 3

1.75 g of L (−)-lactic acid [[(isopropylideneamino)-oxy]methyl]ester, 2.65 g of triphenylphosphine and 2.54 g of p-[(α,α,α-trifluoro-p-tolyl)oxy]-phenol are dissolved at 0° C. in 10 ml of absolute tetrahydrofuran. 1.75 g of azodicarboxylic acid diethyl ether are added dropwise to the solution while cooling. After completion of the addition, the mixture is stirred for 0.5 hour, then poured into 100 ml of water, extracted twice with 50 ml of water each time, dried over anhydrous sodium sulphate and evaporated. The residue is chromatographed on a 20-fold amount of silica gel with n-hexane/ethyl acetate (4:1) and the eluate is evaporated. The residue is crystallised from diethyl ether/n-hexane and there is obtained D-2-[p-[($\alpha,\alpha,\alpha$-trifluoro-p-tolyl)oxy]phenoxy]-propionic acid [[(isopropylideneamino)oxy]methyl]-ester; melting point 85° C.; $[\alpha]_D^{20} = +10.9°$ (c=1.33% in chloroform).

EXAMPLE 4

This Example illustrate the preparation of the starting materials of formulae VI and VIII.

(A) Compounds of formula VIII:

100 g (0.03 mol) of 2-[p-[($\alpha,\alpha,\alpha$-trifluoro-p-tolyl)oxy]phenoxy]-propionic acid and 252 g (3.0 mol) of sodium bicarbonate are suspended in 2.5 liters of dimethyl sulphoxide and thereafter treated slowly with 336.5 ml (3.0 mol) of tert.butyl bromide. The mixture is stirred at room temperature overnight. The mixture, including the separated thick precipitate, is subsequently taken up in 5 liters of ethyl acetate. The ethyl acetate solution is washed twice with 1 liter of water, dried over sodium sulphate and evaporated. The residue is chromatographed on a 10-fold amount of silica gel with hexane/ethyl acetate (7:1) and the eluate is evaporated. There is obtained 2-[p-[($\alpha,\alpha,\alpha$-trifluoro-p-tolyl)oxy]-phenoxy]-propionic acid [(methylthio)methyl]ester in the form of an oil.

In analogous procedures, the following (methylthio)methyl esters of formula VIII are prepared:

(a) from D-2-[p-[($\alpha,\alpha,\alpha$-trifluoro-p-tolyl)oxy]phenoxy]-propionic acid there is obtained D-2-[p-[($\alpha,\alpha,\alpha$-trifluoro-p-tolyl)oxy]phenoxy]-propionic acid [(methylthio)methyl]ester; melting point 47°-48° C.; $[\alpha]_D^{22} = +31.24°$ (c=1.58% in chloroform):

(b) from D-2-[p-(p-chlorophenoxy)phenoxy]-propionic acid there is obtained D-2-[p-(p-chlorophenoxy)-phenoxy]-propionic acid [(methylthio)methyl]ester; melting point 75° C.; $[\alpha]_D^{22} = +50.54°$ (c=1.34% in chloroform);

(c) from 2-[p-(o,p-dichlorophenoxy)phenoxy]-propionic acid there is obtained 2-[p-(o,p-dichlorophenoxy)phenoxy]-propionic acid [(methylthio)methyl]ester; melting point 54° C.;

(d) from D-2-[p-(p-bromophenoxy)phenoxy]-propionic acid there is obtained 2-[p-(o,p-dichlorophenoxy)phenoxy]-propionic acid [(methylthio)methyl]-ester; melting point 83°-87° C.; $[\alpha]_D^{22} = +45.52°$ (c=1.81% in chloroform);

(e) from D-2-[p-(p-iodophenoxy)phenoxy]-propionic acid there is obtained D-2-[p-(p-iodophenoxy)phenoxy]-propionic acid [(methylthio)methyl]ester; melting point 71°-74° C.; $[\alpha]_D^{22} = +41.39°$ (c=1.43% in chloroform).

(B) Compounds of formula VI:

40 g (0.096 mol) of 2-[p-[($\alpha,\alpha,\alpha$-trifluoro-p-tolyl)oxy]phenoxy]-propionic acid [(methylthio)methyl]ester are dissolved in 120 ml of acetone/water (5:1) and treated slowly with 192 ml of a 30% solution of hydrogen peroxide. 96 ml of ammonium molybdate solution (35.2 g of ammonium molybdate in 96 ml of water) are added dropwise to the mixture which is cooled with an ice-bath. The mixture is stirred at room temperature for 2 hours. It is then extracted several times with ether, the ether extract is washed with sodium dithionite solution and the solution is again washed neutral with eight 100 ml portions of saturated sodium chloride solution and subsequently with five 100 ml portions of water. The mixture is treated with active carbon, filtered and evaporated. The residue is recrystallised from methylene chloride/n-hexane. There is obtained 2-[p-[($\alpha,\alpha,\alpha$-trifluoro-p-tolyl)oxy]phenoxy]-propionic acid [(methylsulphonyl)methyl]ester which melts at 87°-88° C.

In analogous procedures, the following (methylsulphonyl)methyl esters of formula VI are prepared:

(a) from D-2-[p-[($\alpha,\alpha,\alpha$-trifluoro-p-tolyl)oxy]phenoxy]-propionic acid [(methylthio)methyl] ester there is obtained D-2-[p-[($\alpha,\alpha,\alpha$-trifluoro-p-tolyl)oxy]phenoxy]-propionic acid [(methylsulphonyl)methyl] ester; melting point 79°-82° C.; $[\alpha]_D^{20} = +40.77°$ (c=1.66% in chloroform);

(b) from 2-[p-[($\alpha,\alpha,\alpha$-trifluoro-p-tolyl)oxy]phenoxy]-propionic acid [(phenylthio)methyl ester there is obtained 2-[p-[($\alpha,\alpha,\alpha$-trifluoro-p-tolyl)oxy]phenoxy]-propionic acid [(phenylsulphonyl)methyl]ester; melting point 89°-92° C.;

(c) from D-2-[p-(p-chlorophenoxy)phenoxy]-propionic acid [(methylthio)methyl] ester there is obtained D-2-[p-(p-chlorophenoxy)phenoxy]-propionic acid [(methylsulphonyl)methyl] ester; melting point 81°-83° C.; $[\alpha]_D^{22} = +43.42°$ (c=1.02% in chloroform);

(d) from 2-[p-(o,p-dichlorophenoxy)phenoxy]-propionic acid [(methylthio)methyl] ester there is obtained 2-[p-(o,p-dichlorophenoxy)phenoxy]-propionic acid [(methylsulphonyl)methyl] ester; melting point 95° C.;

(e) from D-2-[p-(p-bromophenoxy)phenoxy]-propionic acid [(methylthio)methyl] ester there is obtained D-2-[p-(p-bromophenoxy)phenoxy]-propionic acid [(methylsulphonyl)methyl] ester; melting point 84°-87° C.; $[\alpha]_D^{22} = +39.20°$ (c=1.43% in chloroform);

(f) from D-2-[p-(p-iodophenoxy)phenoxy]-propionic acid [(methylthio)methyl] ester there is obtained D-2-[p-(p-iodophenoxy)phenoxy]-propionic acid [(methylsulphonyl)methyl] ester; melting point 121°-123° C.; $[\alpha]_D^{22} = +37.91°$ (c=2.66% in chloroform).

EXAMPLE 5

153 ml (1.1 mol) of tert.butyl bromide are slowly added dropwise to a suspension of 10 g (0.11 mol) of L (+)-lactic acid and 94.2 g (1.1 mol) of sodium bicarbonate in 200 ml of dimethyl sulphoxide. The mixture is stirred for 48 hours, then poured into 1 liter of water and extracted twice with 100 ml of ethyl acetate each time. The organic phase is back-washed three times with 200 ml of water each time and subsequently evaporated. The crude product is chromatographed on a 20-fold amount of silica gel with n-hexane/ethyl acetate (4:1) and the eluate is evaporated. There are obtained 5.7 g of L (−)-lactic acid [(methylthio)methyl] ester; $[\alpha]_D^{20} = -39.27°$ (c=1.3% in chloroform).

The foregoing ester can also be obtained by heating 11.2 g of L (+)-sodium lactate, 0.5 g of 15-crown-5, 9.25 g of chlorodimethyl sulphide and a trace of sodium iodide in 100 ml of absolute acetonitrile at the reflux temperature of the mixture. After 6 hours, the mixture is poured into water and worked-up in the manner described in the preceding paragraph. There are obtained 6.1 g of L (−)-lactic acid [(methylthio)methyl] ester; $[\alpha]_D^{20} = -38.5°$ (c=0.69% in chloroform).

2.55 g (0.01 mol) of p-[($\alpha,\alpha,\alpha$-trifluoro-p-tolyl)-oxy]-phenol, 1.5 g (0.01 mol) of L (−)-lactic acid [(methylthio)methyl] ester and 2.63 g (0.01 mol) of triphenylphosphine are placed in 10 ml of absolute tetrahydrofuran and the mixture is cooled to 0° C. While cooling there is added dropwise 0.011 mol of azodicarboxylic acid diethyl ester, the yellow colour of this ester disappearing during the addition. The mixture is then stirred at room temperature for 30 minutes, poured into 100 ml of water, extracted twice with 50 ml of ethyl acetate each time and the organic phase is washed neutral with water. The ethyl acetate solution is then evaporated, the residue is chromatographed on a 20-fold amount of silica gel with n-hexane/ethyl acetate (9:1) and the eluate is evaporated. After crystallisation from diethyl ether/n-hexane, there are obtained 2.1 g of D-2-[p-[($\alpha,\alpha,\alpha$-trifluoro-p-tolyl)oxy]phenoxy]-propionic acid [(methylthio)methyl] ester; melting point 52° C.; $[\alpha]_D^{20} = +46.87°$ (c=0.65% in chloroform).

EXAMPLE 6

To 100 ml of 36% formalin at 10° C. are added dropwise while cooling 100 ml of piperidine and thereupon 73 g of acetone oxime as well as 75 g of potassium carbonate. The mixture is stirred at room temperature overnight, then taken up in ethyl acetate and the aqueous phase is separated. The organic phase is evaporated, the residue is taken up in acetone and treated dropwise while cooling with 65 ml of methyl iodide, whereafter the product slowly crystallises out. After a further 10 hours, the product is filtered off. There are obtained 291 g of N-[(isopropylideneamino)oxy]-N-methyl-piperidinium iodide; melting point 132°-133° C.

EXAMPLE 7

1.1 g of sodium lactate, 3.5 g of N-[(isopropylideneamino)oxy]-N-methyl-piperidinium iodide and 0.1 g of 15-crown-5 in 10 ml of diglycol dimethyl ether are heated at 110° C. under nitrogen for 4 hours. The mixture is then poured into 50 ml of water and extracted three times with ethyl acetate. The organic phase is washed four times with water and subsequently evaporated. After chromatograhy of the residue on a 10-fold amount of silica gel with n-hexane/ethyl acetate (1:1) and evaporation of the eluate, there is obtained 0.35 g of L (−)-lactic acid [[(isopropylideneamino)oxy]methyl] ester; $[\alpha]_D^{20} = -1.2°$ (c=1.50% in chloroform).

EXAMPLE 8

This Example illustrates the preparation of an emulsifiable concentrate with a compound of this invention.
The following ingredients are admixed

| Ingredient | Amount |
| --- | --- |
| Compound of the formula I | 500 g |
| Condensation products of an alkyl-phenol and ethylene oxide; calcium dodecylbenzenesulphonate | 100 g |
| Epoxidized soya oil with an oxirane oxygen content of ca. 6% | 25 g |
| Butylated hydroxytoluene | 10 g |
| Xylene | to 1 liter |

EXAMPLE 9

This Example illustrates the herbicidal activity of a compound of this invention.
Sufficient active ingredient of 2-[p-[($\alpha,\alpha,\alpha$-trifluoro-p-tolyl)oxy]phenoxy]-propionic acid [[(isopropylideneamino)oxy]methyl] ester (Compound A in the following Tables), is dissolved in acetone to form a 2% solution. When insoluble active ingredients are used, they are formulated as wettable powders which contain kaolin as the inert diluent.

Prior to spraying, the solution is diluted with water to a concentration sufficient to provide, on spraying application, 312 g of active ingredient (a.i.) per hectare.

The compounds were evaluated on *Alopercurus myosuroides*, *Digitaria floridana* and *Avena fatua*.

The test plants were sprayed in a greenhouse where a 16 hour day was simulated by use of mercury vapor lamps. The plants were evaluated for percent necrosis three weeks after spraying. Necrosis is a measurement of the amount of damage to a plant. 100% necrosis corresponds to complete destruction of the plant. The results are tabulated below.

TABLE I

| Active Ingredient | Dosage, g a.i/ha | % Necrosis | | |
| --- | --- | --- | --- | --- |
| | | *Alopecurus myosuroides* | *Digitaria floridana* | *Avena fatua* |
| A | 312 | 100 | 100 | 100 |

Solvent effects, where present, were compensated for by use of the "Abbott formula". The "Abbott formula" is described in Journal Econom. Entomology 18, 265-267 (1925).

EXAMPLE 10

This Example illustrates the effect of active compounds of this invention on cotton var. Stoneville 7A.

Formulations, each containing an active ingredient to be tested, were prepared by admixing the following ingredients.

| Ingredient | Amount |
| --- | --- |
| Active compound | 250 g/l |
| NMP | 300 g/l |
| Tensiofix B 7425 | 100 g/l |
| Phenyl sulfonate CA | 25 gl |
| Shellsol AB | to 1 liter |

0.08% of a wetting agent (Nonoxynol) was added to the formulation prior to spraying.

Cotton test plants, at the 2 leaf stage, were sprayed in a greenhouse at a rate of 1000 l/ha.

Ten days after spraying, the plants were evaluated for percent necrosis. Results are tabulated below.

TABLE II

| Active Ingredient | Dosage, g. a.i./ha | % Necrosis |
| --- | --- | --- |
| A | 0.62 | 0 |
| A | 1.25 | 0 |
| H | 1.25 | 22 |

Compound H is D-2-[p-(p-trifluoromethylphenoxy)-phenoxy]-propionic acid methyl ester.

EXAMPLE 11

This Example illustrates the effect of active compounds of this invention on soybeans var. Hood.

Formulations, each containing an active ingredient to be tested, were prepared by admixing the following ingredients.

| Ingredient | Amount |
|---|---|
| Active compound A | 250 g/l |
| NMP | 300 g/l |
| Tensiofix B 7425 | 100 g/l |
| Phenylsulfonate CA | 25 g/l |
| Shellsol AB | to 1 liter |

0.08% of a wetting agent (Nonoxynol) was added to each formulation prior to spraying.

Soybean plants, at the 2 trifoliate leaf stage, were sprayed in a greenhouse at a rate of 1000 l/ha.

Two weeks after treatment the plants were evaluated for percent necrosis. Results are tabulated below.

TABLE III

| Active Ingredient | Dosage g a.i./ha | % Necrosis |
|---|---|---|
| A | 0.62 | 0 |
| A | 1.25 | 0 |

The notations NMP, Tensiofix B 7425, Phenylsulfonate CA, Shellsol AB and Nonoxynol used in the above Examples 10 and 11 have the following significance:

NMP: N-methyl-2-pyrrolidone.

Tensiofix B 7425: Emulsifier consisting of 60 parts of a block polymerisate of ethylene oxide and propylene oxide, 20 parts of the calcium salt of a branched-chain dodecylbenzenesulfonic acid and 20 parts of a solvent mixture of isobutanol and $C_{10}$-alkylbenzenes.

Phenylsulfonate CA: Mixture of 70 parts of the calcium salt of a branched-chain dodecylbenzenesulfonic acid and 30 parts of a solvent mixture of isobutanol and $C_{10}$-alkylbenzenes.

Shellsol AB: Solvent consisting of a mixture of $C_{10}$-alkylbenzenes.

Nonoxynol: Condensation product of nonylphenol and ethylene oxide.

We claim:

1. A compound of the formula

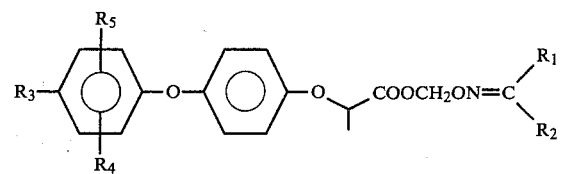

wherein $R_1$ is hydrogen, alkyl of from 1 to 6 carbon atoms or phenyl, $R_2$ is alkyl of from 1 to 6 carbon atoms, alkenyl of from 2 to 6 carbon atoms, alkynyl of from 2 to 6 carbon atoms or phenyl, or $R_1$ and $R_2$ together with the carbon atom to which they are attached form a cycloalkane ring with 4 to 10 carbon atoms which is unsubstituted or is mono-, di- or tri-substituted with alkyl of from 1 to 3 carbon atoms, $R_3$ is halogen, trifluoromethyl or nitro and $R_4$ and $R_5$ each is hydrogen or halogen.

2. A compound according to claim 1, wherein the cycloalkane ring contains 4 to 6 carbon atoms.

3. A compound according to claim 2, wherein $R_1$ is a methyl or ethyl group.

4. A compound according to claim 2, wherein $R_2$ is a methyl, ethyl or phenyl group.

5. A compound according to claim 2 wherein $R_3$ is chlorine or trifluoromethyl.

6. A compound according to claim 2 wherein $R_4$ is a hydrogen.

7. A compound according to claim 2 wherein $R_5$ represents a hydrogen atom.

8. The compound of claim 1, 2-[p-[($\alpha,\alpha,\alpha$-Trifluoro-p-tolyl)oxy]phenoxy]-propionic acid[[(isopropylideneamino)oxy]methyl]ester.

9. The compound of claim 1, 2-[p-(p-Chlorophenoxy)phenoxy]-propionic acid[[(isopropylideneamino)oxy]methyl]ester.

10. The compound according to claim 2 selected from the group consisting of:

D-2-[p-[($\alpha,\alpha,\alpha$-Trifluoro-p-tolyl)oxy]phenoxy]-propionic acid[[(isopropylideneamino)oxy]methyl]ester, D-2-[p-[($\alpha,\alpha,\alpha$-trifluoro-p-tolyl)oxy]phenoxy]-propionic acid[[($\alpha$-methylbenzylideneamino)oxy]methyl]ester, D-2-[p-(p-chlorophenoxy)phenoxy]-propionic acid[-[(isopropylideneamino)oxy]methyl]ester 2-[p-(o,p-dichlorophenoxy)phenoxy]-propionic acid[-[(isopropylideneamino)oxy]methyl]ester 2-[p-(o,p-dichlorophenoxy)phenoxy]-propionic acid[-[($\alpha$-methyl-benzylideneamino)oxy]methyl]ester, D-2-[p-(p-bromophenoxy)phenoxy]-propionic acid[-[(isopropylideneamino)oxy]methyl]ester, D-2-[p-[($\alpha,\alpha,\alpha$-trifluoro-p-tolyl)oxy]phenoxy]-propionic acid[[(cyclopentylideneamino)oxy]methyl]ester, D-2-[p-[($\alpha,\alpha,\alpha$-trifluoro-p-tolyl)oxy]phenoxy]-propionic acid[[(cyclohexylideneamino)oxy]methyl]ester, D-2-[p-[($\alpha,\alpha,\alpha$-trifluoro-p-tolyl)oxy]phenoxy]-propionic acid[[(benzylideneamino)oxy]methyl]ester, D-2-[p-[($\alpha,\alpha,\alpha$-trifluoro-p-tolyl)oxy]phenoxy]-propionic acid[[(sec.butylideneamino)oxy]methyl]ester and D-2-[p-[($\alpha,\alpha,\alpha$-trifluoro-p-tolyl)oxy]phenoxy]-propionic acid[[(1-pentylhexylideneamino)oxy]methyl]ester.

11. The compound according to claim 1 selected from the group consisting of:

D-2-[p-(p-Iodophenoxy)phenoxy]-propionic acid[-[(isopropylideneamino)oxy]methyl]ester, D-2-[p-[($\alpha,\alpha,\alpha$-trifluoro-p-tolyl)oxy]phenoxy]-propionic acid[[(3,3,5-trimethylcyclohexylideneamino)oxy]methyl]ester and D-2-[p-[($\alpha,\alpha,\alpha$-trifluoro-p-tolyl)oxy]phenoxy]-propionic acid[[(1,3-dimethyl-2-butenylideneamino)oxy]methyl]ester.

12. The D-isomers of the compounds of formula I according to claim 1.

13. The D-isomers of the compounds of formula I according to claim 2.

14. A herbicidal composition which comprises an inert carrier material and, as the active ingredient, an amount of one or more of the compounds of claim 1 which is effective as a herbicide.

15. A herbicidal composition of claim 14, wherein the cycloalkane ring contains 4–6 carbon atoms.

16. The herbicidal composition of claim 15 wherein the active ingredient is 2-[p-[($\alpha,\alpha,\alpha$-trifluoro-p-tolyl)oxy]phenoxy]-propionic acid[[(isopropylideneamino)oxy]methyl]ester.

17. The herbicidal composition of claim 15 wherein the active ingredient is 2-[p-(p-chlorophenoxy)phenoxy]-propionic acid[[(isopropylideneamino)oxy]methyl]ester.

18. A herbicidal composition of claim 14, wherein the D-isomer is used as the active ingredient.

19. A method for combatting weeds which comprises applying, to the locus to be protected, a herbicidally effective amount of the composition of claim 14.

20. A method for combatting weeds which comprises applying, to the locus to be protected, a herbicidally effective amount of the composition of claim 15.

21. A method for combatting weeds which comprises applying, to the locus to be protected, a herbicidally effective amount of the composition of claim 16.

22. A method for combatting weeds which comprises applying, to the locus to be protected, a herbicidally effective amount of the composition of claim 17.

23. A method for combatting weeds which comprises applying, to the locus to be protected, a herbicidally effective amount of the composition of claim 18.

* * * * *